(12) United States Patent
Aven et al.

(10) Patent No.: US 6,387,848 B1
(45) Date of Patent: *May 14, 2002

(54) NON-AQUEOUS CONCENTRATED SPREADING OIL COMPOSITION

(75) Inventors: Michael Aven, Mainz (DE); Hideaki Hasui, Aichi Pref.; Masatoshi Motoyoshi, Toyohashi, both of (JP)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/716,194

(22) Filed: Nov. 17, 2000

(51) Int. Cl.$^7$ ............... A01N 63/00; A01N 43/36; A01N 43/02; A01N 43/64; A01N 43/40
(52) U.S. Cl. ............... 504/118; 504/133; 504/134; 504/138; 504/140; 504/246; 504/247
(58) Field of Search ............... 514/248; 504/118, 504/134, 138, 246, 140, 133, 247

(56) References Cited

U.S. PATENT DOCUMENTS

| | | | |
|---|---|---|---|
| 3,888,654 A | 6/1975 | Abramitis | 71/78 |
| 3,996,375 A | 12/1976 | Frensch et al. | 424/276 |
| 4,567,263 A | 1/1986 | Eicken et al. | 544/263 |
| 5,466,693 A | 11/1995 | Warrington et al. | 514/269 |
| 5,593,996 A | 1/1997 | Pees et al. | 514/258 |
| 5,631,210 A | 5/1997 | Tseng | 504/282 |
| 5,731,264 A | 3/1998 | Narayanan et al. | 504/116 |
| 5,948,783 A | 9/1999 | Pees et al. | 514/258 |
| 5,981,534 A | 11/1999 | Pfrengle et al. | 514/258 |
| 5,985,883 A | 11/1999 | Pees | 514/258 |
| 5,986,135 A | 11/1999 | Pfrengle et al. | 564/303 |
| 6,117,865 A | 9/2000 | Pees | 514/212.01 |
| 6,117,876 A | 9/2000 | Pees et al. | 514/258 |
| 6,124,301 A | 9/2000 | Aven et al. | 514/258 |
| 6,165,940 A | * 12/2000 | Aven | 504/118 |
| 6,204,269 B1 | 3/2001 | Pfrengle et al. | 514/258 |
| 6,242,451 B1 | 6/2001 | Pees | 514/258 |
| 6,255,309 B1 | 7/2001 | Pees et al. | 514/256 |

FOREIGN PATENT DOCUMENTS

| | | | |
|---|---|---|---|
| EP | 206987 | 12/1986 | A01N/25/02 |
| EP | 382375 | 8/1990 | C07D/239/52 |
| EP | 0415569 B1 | 3/1991 | |
| EP | 447004 | 9/1991 | C07D/213/81 |
| EP | 0456198 A | 11/1991 | |
| EP | 0933025 A1 | 8/1999 | |
| JP | 06009301 | 1/1994 | |
| WO | 9816102 | 4/1998 | |

* cited by examiner

*Primary Examiner*—Alton Pryor
(74) *Attorney, Agent, or Firm*—Charles F. Costello

(57) ABSTRACT

A non-aqueous, stable concentrated single-phase spreading oil (SO) formulation is disclosed. The SO formulation has a compound of formula I

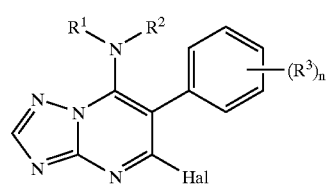

as the active ingredient, and at least one plant oil and polar aprotic organic solvent. Optionally, the SO formulation can also have at least one methylated plant oil. The SO formulation is useful as a blasticide in an aquatic environment of rice plants.

12 Claims, No Drawings

NON-AQUEOUS CONCENTRATED SPREADING OIL COMPOSITION

BACKGROUND OF THE INVENTION

This invention concerns a non-aqueous, storage stable spreading oil (SO) formulation for crop protection active compounds and their use for combating pests, in particular for use in the application of a pesticide to aquatic environments.

However, hitherto pesticides have usually been applied to paddy-fields in the form of soluble, dispersible or absorbent granules which release the active ingredient into the water, or pour-on liquids, in particular emulsifiable concentrate formulations which disperse the active ingredient on the surface of the water (e.g. EP 0 206 987).

The European Patent Application EP 0 415 569 suggests a fungicidal composition for application to an aquatic environment comprising a solid carrier, fungicidal azoxystrobin (EP 0 382 375) as active ingredient and an oil in which said active ingredient is miscible or in which it is capable of being dispersed.

It is well known that the efficacy of plant protection agent can be higher if the active ingredient is applied in dissolved form rather than in a particulate form. One environmentally friendly way to apply an active ingredient in such a form would be dissolved in a plant oil. Unfortunately, most plant protection agents do not exhibit high solubilities in plant oils.

In view of an easy and safe handling and the necessity to improve the efficacy of plant protection agents, it is desirable to develop SO formulations for application in paddy-fields which contain comparably high concentrations of plant protection agents in a spreadable oil.

SUMMARY OF THE INVENTION

The present invention relates to a single-phase non-aqueous, concentrated SO for application of crop protection active compounds in aquatic environments comprising (a) 15 to 400 g/L of one or more crop protection active compounds
(b) 300 to 700 g/L of one or more plant oils;
(c) 30 to 200 g/L of one or more polar aprotic organic solvents;
(d) optionally one or more methylated plant oils;

wherein the sum of all ingredients in the formulation adds up to one liter. Another aspect of the present invention is a process for the preparation of such a SO formulation.

Furthermore, the invention relates to a method for the control of diseases and/or pests in aquatic environments which comprises treating water with the inventive SO formulation, whereupon an oily film spreads over the water surface and subsequently contacts the plants, which are grown or planted before or later in this aquatic environment with the active ingredient(s) contained in said SO formulation.

Another aspect of the invention is a method for the enhancement of the efficacy of fungicidal triazolopyrimidines (e.g. EP 0 550 113), in particular the compounds of formula I

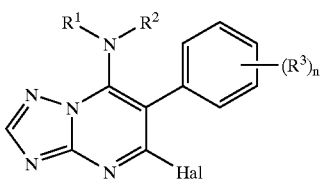

against rice diseases on paddy rice, which comprises applying an effective amount of one or more compounds of formula I dissolved in a mixture which essentially consists of (i) one or more plant oils,
(ii) one or more polar aprotic organic solvents; and
(iii) optionally one or more methylated plant oils;

on the aquatic environment of said rice plants.

Those and other objects and features of the invention will become more apparent from the detailed description set forth hereinbelow.

DETAILED DESCRIPTION OF THE PREFERRED EMBODIMENTS

It has now been found, surprisingly, that stable single-phase non-aqueous SO formulations for application of crop protection active compounds in aquatic environment can be obtained, comprising (a) 15 to 400 g/L of one or more crop protection active (b) 300 to 700 g/L of one or more plant oils;

(c) 30 to 200 g/L of one or more polar aprotic organic solvents;

(d) optionally one or more methylated plant oils;

wherein the sum of all ingredients in the formulation adds up to one liter.

Through use of the SO formulation the biological activity of the active ingredients (a) against pests can be increased compared with conventional formulation types.

The term single-phase as used hereinabove and hereinbelow denotes that the crop protection active compounds (a) are completely dissolved in the homogenous mixture of (a), (b), (c) and optionally (d), without any phase separation.

The term pests as used hereinabove and hereinbelow includes but is not limited to plant pathogens, insects and weeds.

In principle, all crop protection active compounds can be used for the non-aqueous concentrated spreadable oil formulations according to the invention. Lipophilic crop protection active compounds are preferred.

As a rule, crop protection active compounds are used which are essentially insoluble in water and which are less than moderately soluble in a pure plant oil (b). A solubility of less than 100 g/L, in particular less than 50 g/L in pure solvent (b) is preferred.

The compositions of this invention can be applied to the aquatic environment of the plants with different active substances. These active substances can be either fertilizers or agents which donate trace elements or other preparations which influence plant growth or beneficial microorganisms used to improve plant nutrition such as Azetobacter, Rhizobia or azolla or he like. However, they are preferably selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations.

Chemical crop protection compounds which are solid at room temperature are preferred, in particular those with a melting point of higher than 50° C.

Mixtures of different biologically active compounds can have a broader spectrum of activity than a single compound alone. Furthermore, these can exhibit a synergistic effect compared with the single active ingredients. In a preferred embodiment, the formulation of the present invention can be used with a mixture of active ingredients. In the case of mixtures all of the active ingredients (a) are dissolved in the solvent mixture of the SO formulation according to the invention.

Preferred fungicides for use in the compositions of the present invention are the commercially available compounds selected from the group consisting of:

AC 382042, anilazine, azoxystrobin, benalaxyl, benomyl, binapacryl, bitertanol, blasticidin S, bromuconazole, bupirimate, captafol, captan, carbendazim, carboxin, carpropamid, chlorbenzthiazon, chlorothalonil, chlozolinate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, ferimzone, fluazinam, fludioxonil, flumetover, fluquinconazole, flusilazole, flusulfamide, flutolanil, flutriafol, folpet, fuberidazole, furalaxyl, furametpyr, guazatine, hexaconazole, IKF-916, imazalil, iminoctadine, ipconazole, iprodione, isoprothiolane, iprovalicarb, kasugamycin, KH-7281, kitazin P, kresoximmethyl, mepanipyrim, mepronil, metalaxyl, metconazole, methfuroxam, MON 65500, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidone, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, trifloxystrobin, triflumizole, triforine, triticonazole, validamycin A, vinclozolin, XRD-563, zarilamid.

In addition, the formulations according to the invention may contain at least one compound of the following classes of biological control agents such as viruses, bacteria, nematodes, fungi, and other microorganisms which are suitable for the control of insects, weeds or plant diseases, or to induce host resistance in the plants. Examples of such biological control agents are: *Bacillus thuringiensis, Verticillium lecanii, Autographica californica* NPV, *Beauvaria bassiana, Ampelomyces quisqualis, Bacilis subtilis, Pseudomonas fluorescens, Steptomyces griseoviridis* and *Trichoderma harzianum.*

Moreover, the formulations according to the invention may contain at least one chemical agent that induces the systemic acquired resistance in plants such as, for example, isonicotinic acid or derivatives thereof, 2,2-dichloro-3,3-dimethylcylopropylcarboxylic acid or BION.

The SO formulations preferably include derivatives of azolopyrimidines which are disclosed, for example, by European Patent Application EP 0 550 113 or International Patent Application WO 98/46608, in particular the compounds of formula I

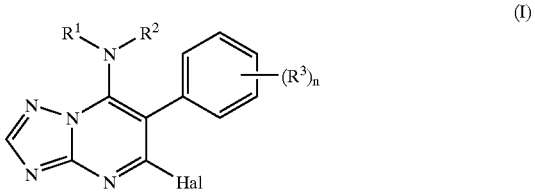

in which
R$^1$ and R$^2$ each independently represent hydrogen or an optionally substituted alkyl, alkenyl, alkynyl, alkadienyl, haloalkyl, aryl, heteroaryl, cycloalkyl, bicycloalkyl or heterocyclyl group, or
R$^1$ and R$^2$ together with the adjacent nitrogen atom represent an optionally substituted heterocyclic ring,
R$^3$ represents a halogen atom or an alkyl or alkoxy group,
n represents an integer from 0 to 5, and Hal represents a halogen atom.

Preferred are the compounds of formula I wherein R$^1$ and R$^2$ together with the interjacent nitrogen atom represent a 4-methylpiperidine ring, or wherein R$^1$ represents a C$_{1-6}$ alkyl, in particular an isopropyl group, a C$_{1-6}$ haloalkyl, in particular a 2,2,2-trifluoroethyl or a 1,1,1-trifluoroprop-2-yl group, or a C$_{3-8}$ cycloalkyl group, in particular a cyclopentyl or cyclohexyl group and R$^2$ represents a hydrogen atom, and/or wherein n is 2 or 3 and the radicals R$^3$ are attached in the 2-, 4- and 6-position and represent a fluorine or chlorine atom or an C$_{1-6}$ alkoxy group.

Particularly preferred are the following azolopyrimidines: 5-chloro-6-(2-chloro-6-fluorophenyl)-7-(4-methylpiperid-1-yl)-[1,2,4]triazolo[1,5-a]pyrimidine coded Azoloyrimidine A, 5-chloro-6-(2-chloro-6-fluorophenyl)-7-(2,2,2-trifluoroethylamino)-[1,2,4]triazolo[1,5-a]pyrimidine coded Azoloyrimidine B and 5-chloro-6-(2,4,6-trifluorophenyl)-7-(1,1,1-trifluoroprop-2-ylamino)-[1,2,4]triazolo[1,5-a] pyrimidine coded Azoloyrimidine C.

Azolopyrimidine C due to the chirality of its 1,1,1-trifluoroprop-2-yl group may be applied as a racemic mixture or in form of an enantiomeric enriched compound, in particular as (S)-enantiomer coded (S)-Azolopyrimidine C.

Most preferred are mixtures of at least one compound of formula I and at least one fungicidally active ingredient which acts as a melanin biosynthesis inhibitor, such as AC 382042.

Preferred herbicides are the commercially available compounds selected from the group consisting of:

2,4-D, 2,4-DB, 2,4-DP, acetochlor, acifluorfen, alachlor, alloxydim, ametrydione, amidosulfuron, asulam, atrazin, azimsulfuron, benfuresate, bensulfuron, bentazon, bifenox, bromobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl fluazifop, fluometuron, fluoroglycofen, fluridone, fluroxypyr, flurtamone, fluthiamid, fomesafen, glufosinate, glyphosate, halosafen, haloxyfop, hexazinone, imazamethabenz, imazamethapyr, imazamox, imazapyr, imazaquin, imazethapyr, ioxynil, isoproturon, isoxaben, isoxaflutole, lactofen, MCPA, MCPP, mefenacet, metabenzthiazuron, metamitron, metazachlor, methyidimron, metolachlor, metribuzin, metsulfuron, molinate, nicosulfuron, norflurazon, oryzalin, oxadiargyl, oxasulfuron, oxyfluorfen, pendimethalin, picloram, pretilachlor, propachlor, propanil, prosulfocarb, pyrazosulfuron, pyridate, qinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclopyr, trifluralin.

Furthermore preferred are the derivatives of aryloxypicolineamides which are disclosed, for example, by European Patent Application EP-A-0 447 004, in particular, N-(4-fluorophenyl) 6-(3-trifluoromethylphenoxy)-pyrid-2-ylcarboxamide having the proposed common name picolinafen.

Examples of insecticidal compounds are alpha-cypermethrin, benfuracarb, BPMC, buprofezine, carbosulfan, cartap, chlorfenvinphos, chlorpyrifos-methyl, cycloprothrin, cypermethrin, esfenvalerate, ethofenprox, fenpropathrin, flucythrinate, flufenoxuron, hydramethyinon, imidacloprid, isoxathion, MEP, MPP, nitenpyram, PAP, permethrin, propaphos, pymetrozine, silafluofen, tebufenozide, teflubenzuron, temephos, terbufos, tetrachlorvinphos and triazamate.

As a rule the non-aqueous SO formulation according to the invention comprises 15 to 400 g/L, preferably 20 to 200 g/L, in particular 25 to 100 g/L of one or more crop protection active compounds.

The plant oils (b) are preferably selected from the group consisting of of olive oil, soybean oil, orange oil and sunflower oil, they are in particular triglycerides or a mixtures of triglycerides including the following fatty acids: palmitic acid, palmoleic acid, stearic fatty, oleic acid, linoleic acid, linoleneic acid.

Preferred are plant oils having a density of less than 1 g/mL, preferably 0.90 g/mL to 0.95 g/mL at 25° C.

Most preferred are plant oils with the following characteristics*:

| Fatty Acid | Olive oil | Sunflower oil | High oleic sunflower oil |
|---|---|---|---|
| palmitic | 12% | ≈1% | 4% |
| palmiloleic | 1% | 7% | ≈1% |
| stearic | 3% | 4% | 4% |
| oleic | 75% | 23% | 80% |
| linoleic | 8% | 64% | 10% |
| linoleneic | 1% | ≈1% | ≈1% |
| Iodine no. | 80–88 | 110–143 | 80–95 |
| Saponification no. | 184–196 | 188–194 | 188–198 |

*given % values are ± 3% and ≥ 0%

As a rule the non-aqueous SO according to the invention comprises 300 to 700 g/L, preferably 350 to 600 g/L, in particular 400 to 500 g/L of one or more plant oils (b).

The polar aprotic solvents (c) used as cosolvents are necessary to increase the amount of the active ingredient. Without these cosolvents, smaller amounts of the active ingredient are soluble in the SO and the resulting formulation may show phytotoxicity due to the increased amount of solvent applied to the plant. Preferred polar solvents are compounds which exhibit a dielectric constant of 2.5 or more at 25° C., in particular from 2.7 to 4.0 at 25° C. and have low solubility in water. Preferred are ketones such as cyclohexanone, lactones such as γ-butyrolactone and amides, in particular cyclic amides as for example N-$C_{1-18}$ alkylpyrrolidones, preferably N-$C_{2-16}$ alkylpyrrolidones, or N-$C_{5-8}$ cycloalkylpyrrolidones. Most preferred are N-octylpyrrolidone and N-dodecylpyrrolidone. In another preferred embodiment of the invention the co-solvent consists essentially of one or more, preferably 2 or 3 dimethyl dicarboxylates of formula

wherein m is 2, 3 or 4.

Particularly preferred is a mixture consisting of glutaric acid dimethyl ester, succinic acid dimethyl ester and adipic acid dimethyl ester, most preferred DBE, which is available from Lemro Chemieprodukte Michael Mrozyk KG, Grevenbroich, Germany.

As a rule the non-aqueous SO according to the invention comprises 30 to 200 g/L, preferably 50 to 150 g/L, in particular 75 to 125 g/L of one or more polar aprotic solvents (c).

Methylated plant oils, which are used as nonpolar, water immiscible cosolvents (d) according to the present invention, are as a rule methyl esters obtainable from medium chained fatty acids by esterification with methanols or by transesterification of the corresponding plant oils preferably in the presence of a lipase. Preferred fatty acids of these plant oils have 5 to 20, in particular 6 to 15 carbon atoms. As a rule they are mixtures of fatty acids having different chain lengths, mixtures in which the main component, i.e. more than 50 percent of said mixture, has 10 carbon atoms are particularly preferred. In a preferred embodiment the methylated plant oil used is the methyl ester of caprylic/capric acid or of capric acid having less than 5 percent of fatty acids having chain lengths different from 10. Particularly preferred methylated plant oils are Witconol® 1095 and Witconol® 2309 which are commercially available from the Witco Corporation, Houston, Tex., USA or Edenor° ME C 6-10 and Edenor® ME C 12 70 which are commercially available from Henkel KGaA, Düsseldorf, Germany. As a rule the non-aqueous SO according to the invention comprises at least 100 g/L, preferably 150 to 450 g/L, in particular 250 to 400 g/L of one or more methylated plant oils (d).

The appropriate relative amounts of active ingredient (a) and the plant oil (b) lie, in accordance with the invention, between 1:50 and 1:1, preferably between 1:30 and 1:5 and, in particular, between 1:20 and 1:10.

Recommended doses for various applications are known for the plant protection active compounds (a) where the efficacy can be enhanced in accordance with the invention. Application in form of a SO formulation as suggested here can (depending on the active ingredient, the solvent and the cosolvent(s) and their amounts) reduce the amount of active ingredient per hectare required in these recommendations by half or more, whereby it becomes possible to control additional diseases at reasonable doses.

An important advantage is the rapid onset and the high persistency of activity on use of the new SO formulation. This enlarges the period for application of the pesticide and makes its use more flexible.

The pesticidal SO formulations according to the present invention can be used protectively and curatively.

In a particularly preferred embodiment according to this invention the non-aqueous SO essentially consists of
 (a) 15 to 400 g/L, preferably 20 to 200 g/L, of one or more crop protection active compounds, in particular a compound of formula I;

(b) 300 to 700 g/L, preferably 350 to 600 g/L, of one or more plant oils selected from the group consisting of olive oil and sunflower oil;

(c) 30 to 200 g/L, preferably 50 to 150 g/L, of at least one polar aprotic solvent, in particular N-octylpyrrolidone or N-dodecylpyrrolidone (d) optionally up to 450 g/L, preferably 200 to 400 g/L of one or more methylated plant oils, in particular methyl esters of caprylic and/or capric acid;

The solvents (b), (c) and (d) and the pesticidal active compounds (a) are processed to the SO formulations according to the invention by well established procedures. For example, the solution can be formed by dissolving (a) in an adequate mixture of (b), (c) and (d), if necessary in the presence of a volatile solvent to aid dissolution.

SO formulations according to the present invention are usually produced so as to obtain a stable liquid product and usually contain 1.5 to 40% w/v active ingredient(s), 30 to 70% w/v of plant oil(s), 3 to 20% w/v of polar aprotic solvent(s), 0 to 45% w/v methylated plant oils, and 0 to 10% w/v of other additives such as defoamers, corrosion inhibitors, stabilizers, penetrants and stickers, and anionic and/or nonionic dispersant(s).

The finished non-aqueous SO formulations according to the invention are stable in storage, i.e. even on storage over a relatively long period. The SOs according to the present invention allow high loadings of one or more pesticidal active ingredients to be included in the formulation and, therefore, offer the advantage of an optimized and easy-to-use formulation of the crop protection active compound.

The solubility of the active ingredients (a) in the formulation according to the invention depends not only on the structure of the active ingredient but also on the amount of the cosolvent (c). The relative amount of active ingredient (a) increases by about 40 to 60% when 10 to 15% cosolvent (c) is incorporated into the formulation.

The SO formulation according to the invention is preferably sprayed or poured onto the surface of the aquatic environment of paddy rice fields, in particular using the so-called Shaker Bottle Application.

The formulation spreads well as a monolayer on the surface of water and sticks to the lipophilic leaf surface of the rice plants.

Solid granules in which the SO formulation according to the invention is adsorbed onto a solid carrier, as for example disclosed e.g. by EP 0 415 569, also lie within the scope of the invention.

The SO formulation as hereinbefore described containing a fungicide as active ingredient (a) preferably has fungicidal effects against one or more of the following diseases: bacterial leaf blight (*Xanthomonas campestris* pv. oryzae), blast (*Pyricularia oryzae*), brown spot (*Cochliobolus miyabeanus*), bakanae disease and foot rot (*Gibberella fujikuroi*), sheath blight (*Rhizoctonia solani*) and seedling blight (*Corticium roffsii*). As used herein the phrase "fungicidal effect" means that the active ingredient displays activity against a fungal disease.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

Examples of non-aqueous SO formulations according to the invention are shown in the following examples 1 to 4:

| Identity of Ingredients used in Examples | | |
|---|---|---|
| Name | Function | Identity |
| Agsol Ex 8 (ISP) | Cosolvent (c) | N-octylpyrrolidone |
| Agsol Ex 12 (ISP) | Cosolvent (c) | N-dodecylpyrrolidone |
| Olive Oil (Mosselman) | Solvent (b) | Triglyceride, mostly oleic fatty acid |
| High Oleic Sunflower Oil (Mosselman) | Solvent (b) | Triglyceride, mostly oleic fatty acid |
| Sunflower Oil (Mosselman) | Solvent (b) | Triglyceride, mostly linoleic fatty acid |
| Witconol ® 1095 (Witco) | Solvent (d) | Technical methyl ester of caprylic/capric acid |
| Witconol ® 2309 (Witco) | Solvent (d) | Technical methyl ester of caprylic/capric acid |

EXAMPLE 1

The following SO formulation according to the invention is prepared by dissolving the active ingredient in a mixture of the solvents (b), (c) and (d)

The following formulation is obtained:

| Ingredient | Concentration |
|---|---|
| (S)-Azolopyrimidine C | 30 g |
| Olive oil | 450 g |
| Agsol Ex 8 | 100 g |
| Witconol 1095 | to 1 L |

The SO formulation exhibits the following properties:

Density=0.912 g/mL; Flash point >83° C.;

No crystals were formed upon storage at 0° C. for 1 week.

EXAMPLE 2

The following SO formulation according to the invention is prepared by dissolving the active ingredient in a mixture of the solvents (b), (c) and (d)

The following formulation is obtained:

| Ingredient | Concentration |
|---|---|
| Azolopyrimidine C | 30 g |
| High Oleic Sunflower oil | 400 g |
| Agsol Ex 8 | 90 g |
| Witconol 2309 | to 1 L |

EXAMPLE 3

The following SO formulation according to the invention is prepared by dissolving the active ingredient in a mixture of the solvents (b), (c) and (d)

The following formulation is obtained:

| Ingredient | Concentration |
|---|---|
| Azolopyrimidine C | 30 g |
| AC 382042 | 100 g |
| Olive oil | 400 g |
| Agsol Ex 12 | 100 g |
| Witconol 1095 | to 1 L |

Example 4

The following SO formulation according to the invention is prepared by dissolving the active ingredient in a mixture of the solvents (b), (c) and (d)

The following formulation is obtained:

| Ingredient | Concentration |
|---|---|
| Fluthiamid | 30 g |
| Olive oil | 450 g |
| Agsol Ex 8 | 150 g |
| Witconol 1095 | to 1 L |

Control of *Pyricularia oryzae*

Paddy-rice plants of the variety "Koshihikari" were grown in nursery boxes, and were transplanted to the greenhouse in plots of 457 cm² (4 plants/pot). 3 days after transplanting, different formulations of (S)-azolopyrimidine C were added to the water. The plants were inoculated with spore solution of *Pyricularia oryzae* at 45 days after treatment with the active ingredient. Untreated plots were included in the test.

A Rice Leaf Blast 52 days after the treatment 63% of the leaf area of the untreated rice plants (controls) were infected with the rice blast disease. The disease level (% infected leaf area) was also assessed in the treated plants, and the efficacy (in %) of the treatment was measured. The effects of the SO formulation according to the invention and a granular formulation are given in Table I.

TABLE 1

Percent rice leaf blast control

| | | control (%) | |
|---|---|---|---|
| Active ingredient | dose (g/ha) | SO 30 g/L (Example 1) | Granules 50 g/kg |
| (S)-Azolopyrimidine C | 50 | 84 | n.t. |
| | 100 | 89 | 78 |
| | 250 | 95 | 86 |
| | 500 | 97 | 90 |
| | 1000 | 98 | 95 |
| | 1500 | n.t. | 97 |
| probenazole Granules 80 g/kg | 2400 | 74 | |

B Rice Panicle Blast 126 day after the treatment 60% of the panicles of the untreated rice plants (controls) were infected with the rice blast disease. The disease level (% infected panicles) was also assessed in the treated plants, and the efficacy (in %) of the treatment was measured. The effects of the SO formulation according to the invention and a granular formulation are given in Table II.

TABLE II

Percent rice danicle blast control

| | | control (%) | |
|---|---|---|---|
| Active ingredient | dose (g/ha) | SO 30 g/L (Example 1) | Granules 50 g/kg |
| (S)-Azolopyrimidine C | 50 | 22 | n.t. |
| | 100 | 44 | 39 |
| | 250 | 67 | 44 |
| | 500 | 78 | 67 |
| | 1000 | 84 | 82 |
| probenazole Granules 80 g/kg | 2400 | 69 | |

These tests clearly prove that a dose reduction of about 50% for equivalent disease control can be achieved with the SO formulation according to this invention compared to a conventional granule formulation.

In addition, phytotoxicity has been negligible at the tested application rates.

Moreover, the inventive SO formulations are more environmentally friendly than conventional formulations and have improved toxicity profiles which renders the handling of these formulation safer.

What is claimed is:

1. A non-aqueous, stable concentrated single-phase spreading oil (SO) formulation for crop protection active compounds comprising (a) 15 to 400 g/L of one or more crop protection active compounds:

(b) 300 to 700 g/L of one or more plant oils;

(c) 30 to 200 g/L of one or more polar aprotic organic solvents selected from the group consisting of N—$C_{1-18}$ alkylpyrrolidone, N—$C_{5-8}$ cycloalkylpyrrolidone, γ-butyrolactone and cyclohexane; and (d) optionally one or more methylated plant oils;

wherein the sum of all ingredients in the formulation adds up to one liter.

2. A SO formulation in accordance with claim 1 containing 100 to 450 g/L of said one or more methylated plant oils (d).

3. A SO formulation in accordance with claim 1 wherein said crop protection active compounds (a) comprise at least one triazolopyrimidine of formula I (I)

in which $R^1$ and $R^2$ each independently represent hydrogen or an optionally substituted alkyl, alkenyl, alkynyl, alkadienyl, haloalkyl, aryl, heteroaryl, cycloalkyl, bicycloalkyl or heterocyclyl group, or R¹ and R² together with the adjacent nitrogen atom represent an optionally substituted heterocyclic ring, R³ represents a halogen atom or an alkyl or alkoxy group, n represents an integer from 0 to 5, and Hal represents a halogen atom.

4. A SO formulation in accordance with claim 1 wherein said plant oil (b) is selected from the group consisting of olive oil, soybean oil, orange oil and sunflower oil.

5. A SO formulation in accordance with claim 1 wherein said plant oil (b) is a triglyceride or a mixture of triglycerides consisting essentially of the following fatty acids: palmitic acid, palmoleic acid, stearic fatty, oleic acid, linoleic acid, linoleneic acid.

6. A SO formulation in accordance with claim 1 wherein the ratio of the crop protection active compounds (a) to said plant oil (b) is between 1:50 and 1:1.

7. A SO formulation in accordance with claim 1 wherein the polar aprotic organic solvents (c) is N-octylpyrrolidone or N-dodecylpyrrolidone.

8. A SO formulation in accordance with claim 2 wherein said methylated plant oil (d) is a $C_{10}$ methylated fatty acid.

9. A SO formulation in accordance with claim 2 wherein said methylated plant oil (d) is a methyl ester obtained from palm kernel oil.

10. A method for the control of diseases and/or pests in aquatic environments which comprises treating water with a SO formulation as claimed in claim 1, whereupon an oily film spreads over the water surface and subsequently contacts the plant with the active ingredient(s) contained in said SO formulation, for said control of diseases and/or pests in aquatic environments.

11. A method for the enhancement of the efficacy of the compounds of formula I

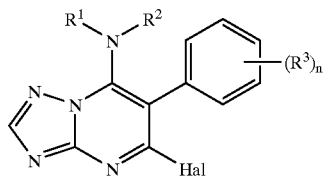

(I)

wherein $R^1$, $R^2$, $R^3$, Hal and n have the meaning given in claim 2, against rice diseases on paddy rice, which comprises applying an effective amount of one or more compounds of formula I dissolved in a mixture which consists essentially of (i) one or more plant oils, (ii) one or more polar aprotic organic solvents; and (iii) optionally one or more methylated plant oils;

on the aquatic environment of said rice plants.

12. A non-aqueous, stable concentrated single-phase spreading oil (SO) formulation for crop protection active compounds comprising (a) 15 to 400 g/L of one or more crop protection active compounds;

(b) 300 to 700 g/L of one or more plant oils;

(c) 30 to 200 g/L of one or more polar aprotic organic solvents selected from a cyclic amide; and (d) optionally one or more methylated plant oils;

wherein the sum of all ingredients in the formulation adds up to one liter.

* * * * *